United States Patent [19]

Chatenever

[11] Patent Number: 4,807,594
[45] Date of Patent: Feb. 28, 1989

[54] ADAPTER ASSEMBLY FOR ENDOSCOPIC VIDEO CAMERA

[75] Inventor: David Chatenever, Santa Barbara, Calif.

[73] Assignee: Medical Concepts, Incorporated, Santa Barbara, Calif.

[21] Appl. No.: 139,785

[22] Filed: Jan. 15, 1988

[51] Int. Cl.⁴ .............................................. A61B 1/04
[52] U.S. Cl. ...................................... 128/4; 350/319; 350/589
[58] Field of Search ............... 128/4, 6; 350/319, 374, 350/588, 589, 590; 358/98

[56] References Cited

U.S. PATENT DOCUMENTS

| | | | |
|---|---|---|---|
| 4,076,018 | 2/1978 | Heckele | 128/6 |
| 4,279,246 | 7/1981 | Chikama | 128/6 |
| 4,323,304 | 4/1982 | Ishii | 128/6 X |
| 4,344,092 | 8/1982 | Miller | 358/98 X |
| 4,355,861 | 10/1982 | Sebald | 350/61 |
| 4,413,278 | 11/1983 | Feinbloom | 358/98 X |
| 4,414,576 | 11/1983 | Randmae | 358/299 |
| 4,439,030 | 3/1984 | Ueda | 128/4 X |
| 4,611,888 | 9/1986 | Prenovitz et al. | 128/6 X |
| 4,621,618 | 11/1986 | Omagari | 128/6 |
| 4,639,772 | 1/1987 | Sluyter et al. | 358/98 |
| 4,697,894 | 10/1987 | Takamura et al. | 350/574 |
| 4,722,000 | 1/1988 | Chatenever | 358/98 |

Primary Examiner—William H. Grieb
Attorney, Agent, or Firm—Elliot N. Kramsky

[57] ABSTRACT

An endoscopic adapter assembly for coupling a video camera head and an endoscope having a proximal end, the adapter includes an ocular adapter for engaging securely the proximal end of the endoscope. An endoscope-engageable portion engages the coupler adapter and a focusing portion is rotatably secured to the endoscope-engageable portion. A camera-engageable portion is rotatably secured to the focusing portion for connecting it to the camera head. The ocular adapter portion includes a window which is complementarily shaped and designed to face and to be aligned with a window of the ocular adapter for maintaining glass-on-glass contact therewith.

35 Claims, 3 Drawing Sheets

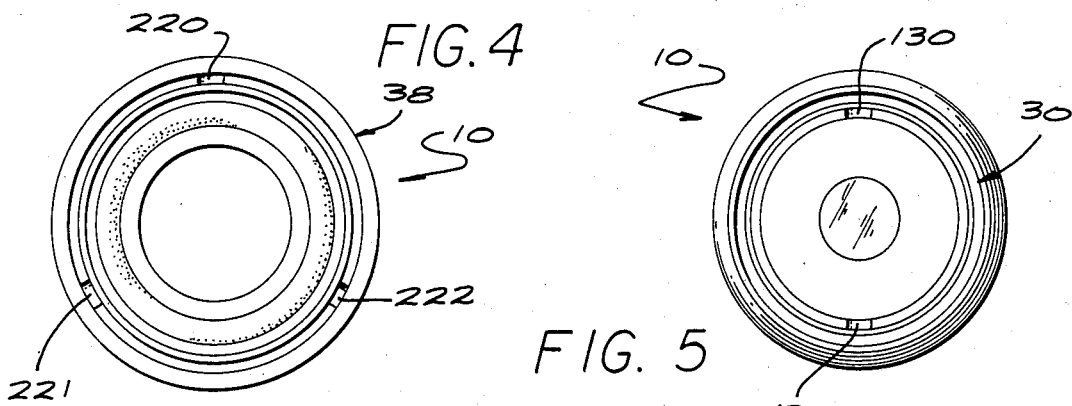
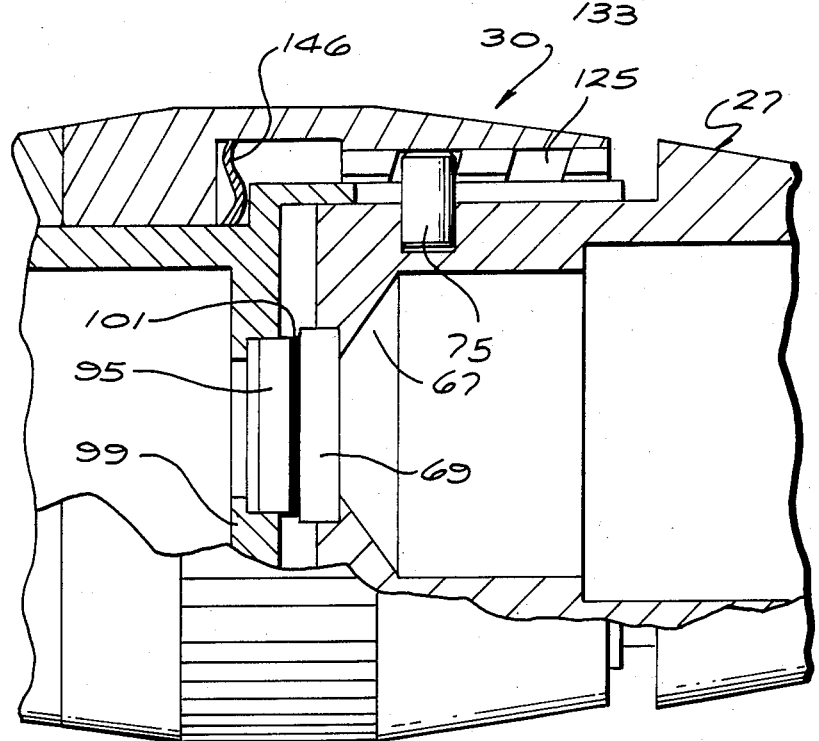
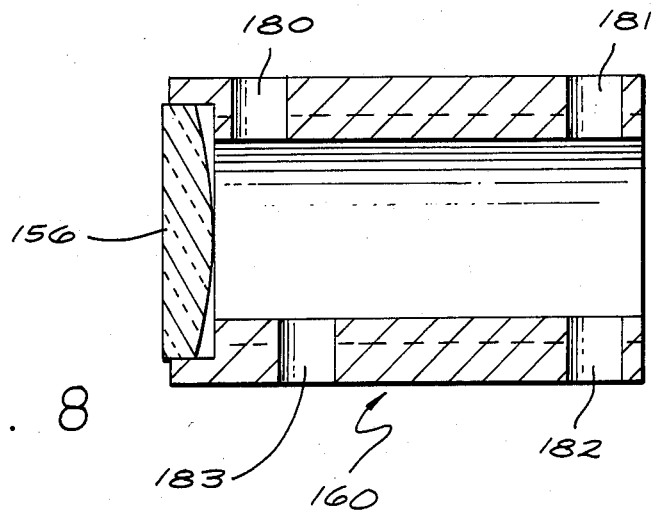

ADAPTER ASSEMBLY FOR ENDOSCOPIC VIDEO CAMERA

BACKGROUND

1. Field of the Invention

The present invention relates in general to devices used in video endoscopy. More particularly, the present invention pertains to a new and improved adapter assembly for connecting an endoscope to a video camera head.

2. Description of the Prior Art

The field of video endoscopy to which the present invention generally relates includes medical diagnostic and therapeutic disciplines which utilize endoscopes to penetrate and to view otherwise inaccessible body cavities, with minimal intrusion and surgical procedures. Conventional endoscopes can generally be categorized into two classes, namely rigid endoscopes and flexible endoscopes. Examples of such endoscopic instruments include the laparoscope, cystoscope, arthroscope, ureterscope, bronchoscope, and colonoscope.

The advent of video endoscopy has enhanced the utility of the endoscope significantly. In this regard, the use of video cameras provides visual protection to the surgeon and promotes his or her comfort during the operation. Therefore, the surgeon can now provide the endoscopic surgery comfortably with less fatigue, and the surgical procedure can be performed relatively fast and efficiently.

The adaption of video camera technology to endoscopy imaging requires means for coupling the conventional endoscopes to a video camera head. There have been various types of endoscope couplers which generally include real image forming optics mounted within a sleeve, as well as means for focusing the optics. Exemplary endoscope couplers and other adapters in the field are described in U.S. Pat. Nos. 4,076,018 to Heckele; 4,279,246 to Chikama; 4,344,092 to Miller; 4,355,861 to Sebald; 4,413,278 to Feinbloom; 4,414,576 to Randmae; 4,439,030 to Veda; 4,621,618 to Omagari; and 4,639,772 to Sluyter, et al.; and Japanese Pat. No. 58-21134 to Nishigaki.

An endoscopic system, as defined for reference purposes throughout the following description, generally includes an endoscope, an optical adapter and a video camera head. Before use, the endoscopic system must be sterilized by soaking or immersion in a sterilizing solution, followed by drying and assembly. However, the viewing clarity of the adapter can be hampered by the trapping of residual liquid particles inside the chambers or cavities formed between the adapter and the endoscope, as well as between the adapter and the video camera head.

The endoscopic system is, therefore, amenable to unavoidable condensation of the liquid particles on the optical surfaces of the adapter. Such condensation is generally caused by the high energy and heat emitted by the source of illumination, which heats the proximal metallic portions of the endoscope. The condensation generally takes place on the relatively cool front window of the optical adapter, which offer a lower moisture-pressure gradient than the surrounding metal surfaces. The resulting reduction in clarity can significantly hinder the physician's diagnostic ability and can limit the physician's ability to perform the necessary surgical procedures.

While various techniques and couplers have been employed to minimize the condensation of the residual fluid particles on the cooler viewing optics, none has proven to be entirely satisfactory. One such coupler is described in U.S. Pat. No. 4,611,888 to Prenovitz, et al., and relates in general to a device for coupling a rigid surgical endoscope to a video camera.

However, while the patented device may have been successful in providing a compact coupler, it suffers from various severe drawbacks which render it less than desirably practical or efficient for modern applications. In this regard, the disclosed coupling device includes front and rear sections which are rotatable relative to one another in order to cause a similar rotation of the endoscope relative to the camera head. The device further includes sealing means which tends to reduce the fogging of the viewing optics. By using the disclosed coupler, the soaking process of the endoscopic system is accomplished as a unitary arrangement.

However, the patented coupler cannot be used readily in arthroscopic procedures or such other similar endoscopic surgeries which require the interchangeability of endoscopes during the surgical procedure. In fact, the disconnection of the patented coupler from the endoscope during the surgical procedure can expose the image forming optics of the endoscopic system to fluids surrounding the surgical wound. Therefore, it appears that in order to prevent contamination, the endoscopic coupler must remain unitarily connected to the endoscope throughout the surgery. Thus, in order to be able to interchange endoscopes during the surgery, one has to utilize several endoscopic systems, each one having its own coupler and camera head. Thus, the use of the patented coupler tends to complicate the endoscopic proceeding rather than to simplify it.

Furthermore, since only the external section of the endoscopic system would be soaked prior to use, while the inner sections would not be sterilized, the uncoupling of the endoscope or the camera head during the surgical proceeding would increase the risk of contamination. An additional drawback of the patented coupler is its inability to be readily focused by the surgeon. Thus, in certain applications, the whole endoscopic system would have to be substituted with another endoscopic system. As a result, the surgical process is periodically disrupted, and is further rendered relatively complex and inefficient.

Therefore, it would be highly desirable to have a new and improved endoscopic adapter assembly for use in video endoscopy to couple an existing adapter to a corresponding camera head. The adapter assembly should substantially minimize, if not completely eliminate condensation on selected viewing optics of the endoscopic system, without compromising its sterility and effectiveness. It should further enable the interchangeability of endoscopes during the surgical procedure, and it should further be readily focusable. Additionally, the adapter assembly should be light in weight, compact, relatively simple to use, and inexpensive to produce.

SUMMARY AND OBJECTS OF THE INVENTION

Briefly, the above and further objects and features of the present invention are realized by providing a new and improved adapter assembly for an endoscopic video camera head. The adapter assembly generally includes an ocular adapter for engaging securely the proximal end of the endoscope. An endoscope-engageable portion engages the ocular adapter, and a focusing portion is rotatably secured to the endoscope-engageable portion. A camera-engageable portion is rotatably secured to the focusing portion for connecting it to the camera head. The ocular adapter portion includes a window which is complementarily shaped and designed to face, and to be aligned with, a window of the endoscope engageable portion for maintaining glass-on-glass contact therewith.

BRIEF DESCRIPTION OF THE DRAWINGS

The above-mentioned and other objects and features of the present invention and the manner of obtaining them will become apparent, and the invention itself will be best understood, by reference to the following description of the embodiment of the invention, taken in conjunction with the accompanying drawings, wherein:

FIG. 4 is a pictorial end view of an endoscopic adapter assembly which forms a part of the endoscopic system of FIG. 1, illustrating an endoscope-engageable portion thereof;

FIG. 5 is a pictorial end view of the endoscopic adapter assembly of FIG. 4, illustrating a camera-engageable portion thereof;

FIG. 7 is an enlarged cross-sectional side elevational view of the ocular adapter and the endoscope-engageable portion, taken on line 7—7 of FIG. 1; and FIG. 8 is an enlarged cross-sectional side elevational view of a lens sleeve which is constructed in accordance with the present invention, and which forms a part of the endoscopic adapter of FIG. 2.

DETAILED DESCRIPTION

Figure 1:
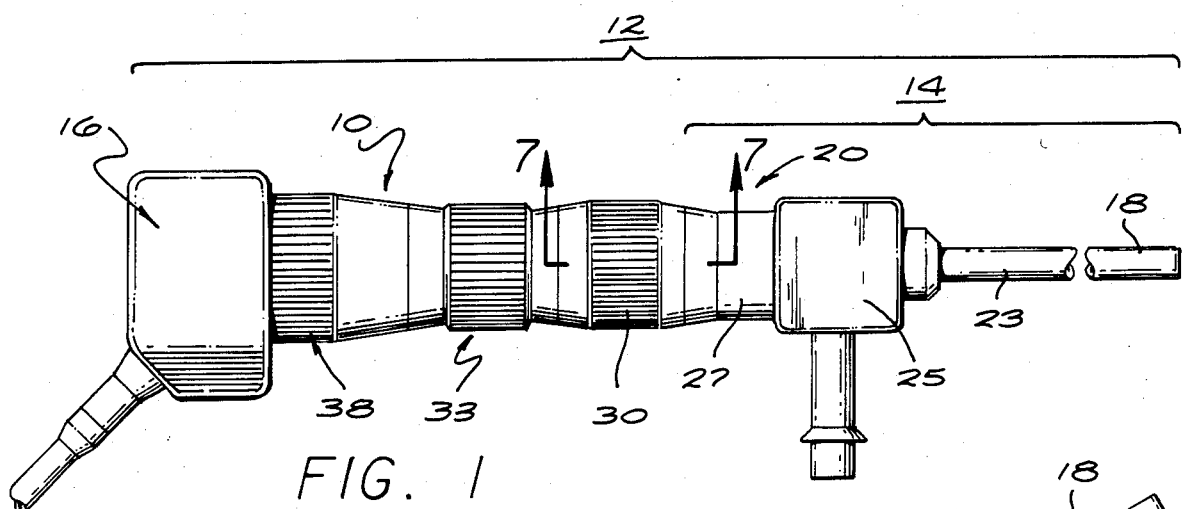
FIG. 1 is a fragmentary pictorial view of an assembled endoscopic system using an adapter assembly which is constructed in accordance with the present invention.
Figure 2:
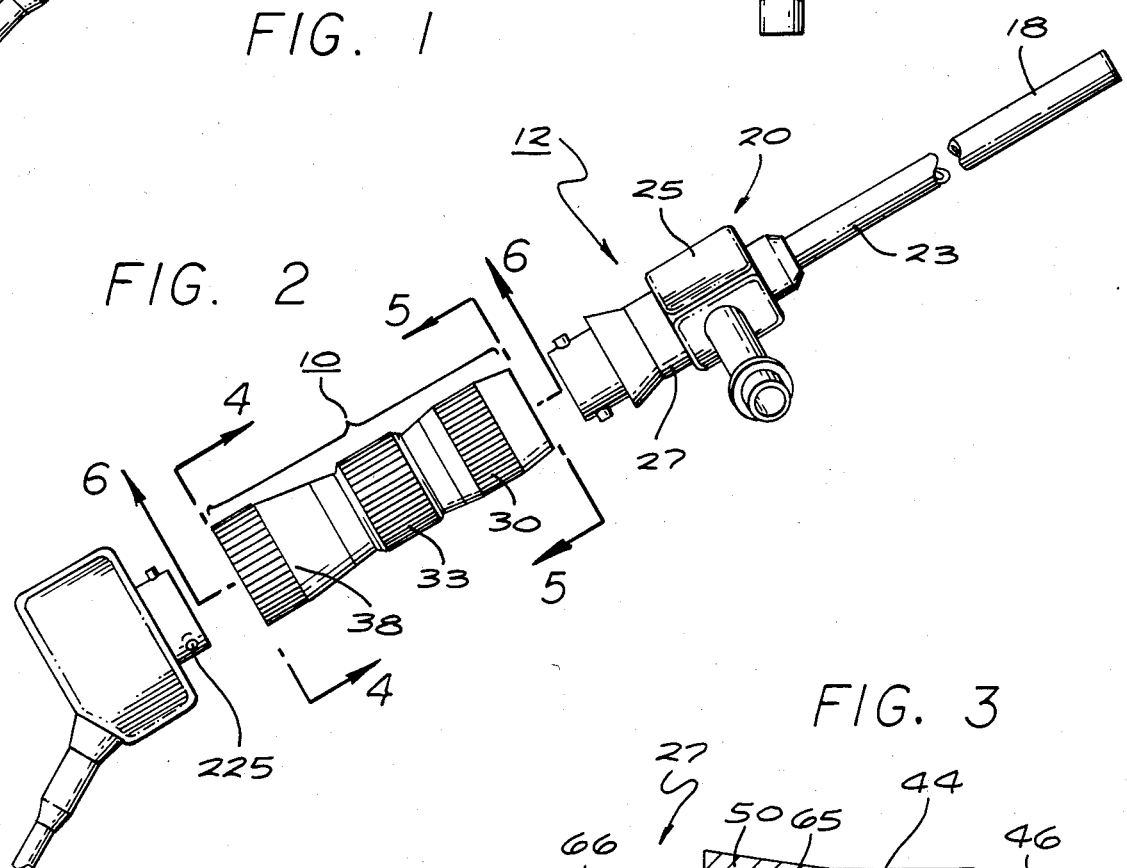
FIG. 2 is an exploded view of the assembled system of FIG. 1 depicting the three components of the endoscopic system (i.e. camera head, optical adapter and endscope)

Referring now to the drawings, and more particularly to FIGS. 1 and 2 thereof, there is illustrated an endoscopic adapter assembly 10 which forms a part of an endoscopic system 12, for coupling an endoscope 14 and a video camera head 16. The endoscope 14 can be of the conventional type, and it generally has a distal end 18, a proximal end 20, and an elongated tubular probe 23. It should, however, be understood that while a rigid tubular probe 23 is herein illustrated, a flexible tubular probe can be used alternatively.

A hub 25 is disposed at the proximal end 20 for interconnecting the probe 23 to the adapter assembly 10 and to a source of illumination. The endoscope 14 further includes viewing optics (not shown) which produce a virtual image of the internal body cavity region being probed. The virtual image is then focused by the adapter assembly 10 on the electronic pick-up device within the camera head 16.

Generally, a conventional endoscope 14 includes an eyepiece (not shown) at its proximal end. The eyepiece typically includes a flared flange for facilitating the visual use of the endoscope 14 by the surgeon. In the preferred embodiment, the present endoscopic system 12 has substituted the conventional eyepiece with a collar or an ocular adapter 27 for securing the endoscope 14 to the adapter assembly 10.

The adapter assembly 10 further includes an endoscope-engageable portion, which is generally indicated at 30, for engaging the ocular adapter 27 in a manner which will be described hereinafter in greater detail. An intermediate or focusing portion 33 has one of its ends rotatably secured to the endoscope-engageable portion for focusing the virtual image produced at the proximal end 20 of the endoscope 14 onto the electronic pick-up device within the camera head 16.

A camera-engageable portion or a camera adapter 38 is rotatably secured to the other end of the focusing portion 33 for connecting fixedly the adapter assembly 10 to the camera head 16. As will be described later, the cameraengageable portion can provide two types of human feedback signals, namely visual and audible signals, for ensuring its proper engagement to the camera head 16.

In use, the eyepiece of the endoscope 14 is detached from its proximal end 20 by unscrewing it. Next, the ocular adapter 27 is connected threadably to the proximal end 20. Subsequently, the endoscope-engageable portion 30 is secured axially to the ocular adapter 27 in accordance with the presently inventive process. Thereafter, the camera head is mated with the camera adapter 38.

Thus, as illustrated in FIG. 1, once the adapter assembly 10 is coupled intermediate the endoscope 14 and the camera head 16, it assumes a unitary compact construction therewith. The new and improved endoscopic adapter assembly 10 allows the focusing of the virtual image at the proximal end 20, and it further enables the axial positioning of the camera head 16 and the endoscope 14 relative to one another.

Figure 3:
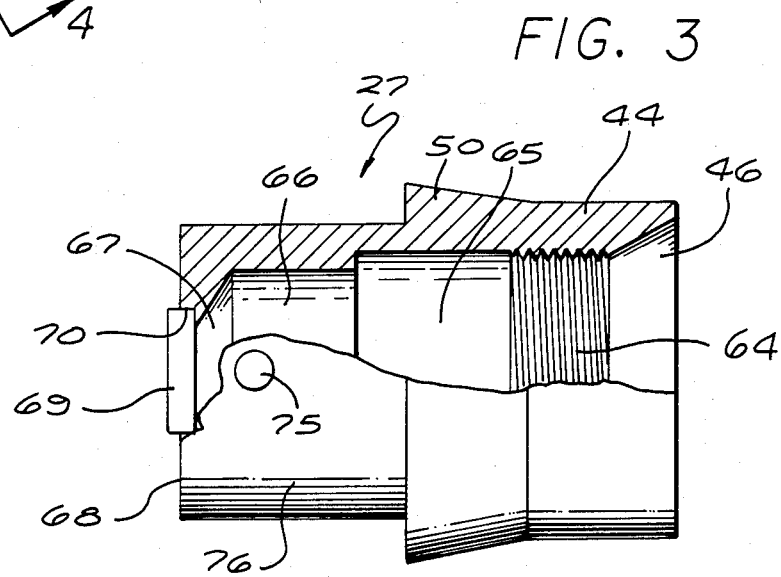
FIG. 3 is an enlarged partially sectional side elevational view of an ocular adapter which forms a part of the endoscopic system of FIG. 1.

Considering now the ocular adapter 27 in greater detail with respect to FIG. 3, it generally mates with the proximal end 20 of the endoscope 14 for protecting its ocular optics. The ocular adapter 27 generally includes an elongated tubular chassis 44 which is hollow throughout its axial length for providing an unobstructed ocular field of vision. The chassis 44 projects radially outwardly into an annularly protruding flange 50, which abuts the endoscope-engageable portion 30. The chassis 44 is generally made of a suitable non-corrosive material such as stainless steel.

The chassis 44 has one of its ends 46 inwardly conically tapered and extending into an internally helically threaded section 64 for engaging the proximal end 20 of the endoscope. A plurality of discrete axially successive internal chambers 65, 66 and 67 extend from the threaded section 64 to the opposite end 68 of the chassis 44. A window 69 is centrally disposed at the end 68 of the chassis 44, at a substantially right angle to the axis thereof. The window 69 is partly recessed within a complementary shaped and sized opening 70, and partly protrudes a relatively short distance between the outermost flat radial surface of the end 68. The window 69 is substantially circular, and it can be made of a suitable transparent material such as glass or sapphire for increased hardness.

A pair of similar pins or studs (only one of which is illustrated in FIG. 3 and indicated at 75) protrudes radially from the outer periphery of the forward section 76 of the chassis 44, at a relatively close distance to the end 69, for attaching to a corresponding coupling mechanism of the endoscope-engageable portion 30. The purpose of the axial protrusion of the window 69 and the structure of the coupling mechanism of the endoscope-engageable portion 30 will become apparent to those skilled in the art after reviewing the following description of the endoscope-engageable portion 30.

Figure 6:
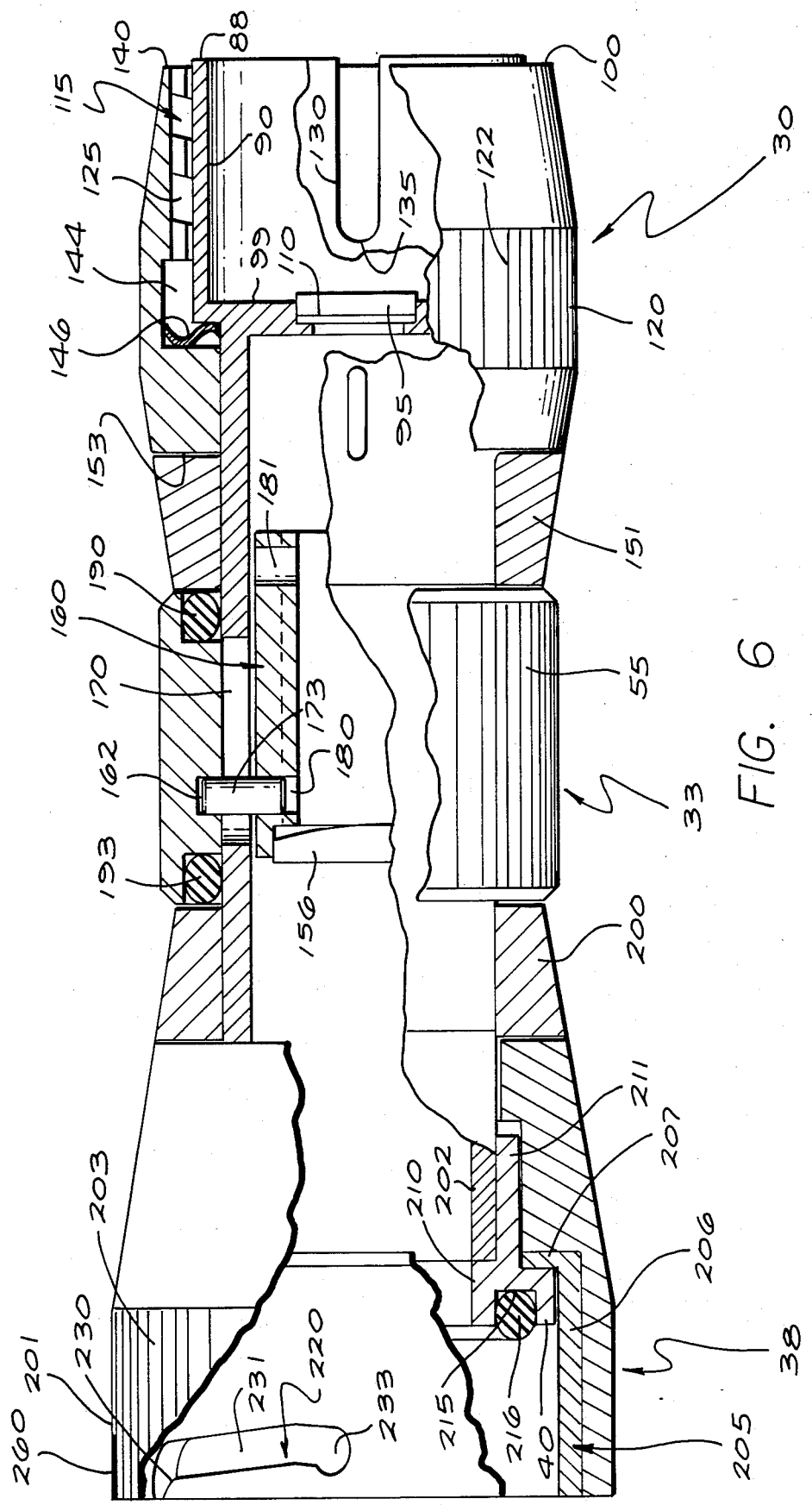
FIG. 6 is an enlarged partially cross-sectional side elevational view of the endoscopic adapter assembly of FIG. 4, taken on line 6—6 of FIG. 2.

Considering now the endoscope-engageable portion 30 in greater detail with respect to FIGS. 4, 6 and 7, it generally includes an elongated tubular chassis 88 which is hollow throughout its axial length, for providing an unobstructed transmission of the visual image produced at the proximal end 20 of the endoscope. The chassis 88 extends throughout the axial length of the endoscope-engageable portion 30 and the focusing portion 33, as well as throughout about one-half the axial length of the camera engageable portion 38. The chassis 88 is made of suitable non-corrosive material such as stainless steel.

The chassis 88 includes a flared annular section 90 which is generally circular in cross-section, and which is complementarily sized and dimensioned to receive the forward section 76 of the ocular adapter chassis 44. While the outer periphery of the forward section 76 can be sized to mate frictionally with the inner periphery of the flared annular section 90, it will become apparent that such friction-tight arrangement is not critical to the reduction or elimination of condensation on the optical surfaces of the adapter assembly 10. In fact, the present invention does not attempt to achieve a liquid-tight sealing engagement between the chassis 88 of the endoscope-engageable portion 30 and the chassis 44 of the ocular adapter 27. Rather, the clarity of the viewing optics will be achieved by glass-on-glass interface.

For the purpose of achieving such glass-on-glass interface, the endoscope-engageable portion 30 includes a window 95 which is centrally housed within the flared annular section 90. The window 95 is secured by known techniques to a transverse annular shoulder portion 99, which extends integrally inwardly from said flared annular section 90, at a substantially right angle to the central axis of the chassis 88. The window 95 is generally circular and is symmetrically aligned relative to the central axis of the chassis 88.

The shoulder 99 and the window 95 are recessed inwardly relative to the open terminal end 100 of the chassis 88 at a distance which is slightly shorter than the axial length of the forward section 76 of the chassis 44 (FIG. 3).

The window 95 protrudes partially from the surface of the shoulder 99 facing the terminal end 100, in order to abut the window 69 and to maintain a glass-on-glass interface therewith. The window 95 is generally similar in design and construction to the window 69, and it is substantially aligned therewith when the endoscope-engageable portion is coupled with the ocular adapter 27.

The glass-on-glass interface of the two windows 69 and 95 is particularly desirable to achieve the desired optical clarity and to minimize, if not to eliminate the condensation on the optical windows of the adapter assembly 10. Thus, by achieving glass-on-glass interface between the windows 69 and 95, the residual irregularly shaped fluid particles on the contacting flat surfaces are compressed into a substantially thin and uniformly distributed film 101 (FIG. 7). As a result, the virtual image formed at the proximal end of the endoscope is transmitted through the ocular adapter 27 and the endoscopic-engageable portion 30, with minimal distortion or refraction, that would have occurred but for the glass-on-glass interface.

The glass-on-glass interface in the present application eliminates the use of conventional degradable liquid-tight seal. In fact, the close proximity of the contacting surfaces of the windows 69 and 95, as well as the thin film 101 which is captured therebetween, render the glass-on-glass arrangement substantially impermeable to external fluid particles.

Additionally, the glass-on-glass interface allows the interchangeability of the endoscope during the surgical procedure, since the clarity of vision is ensured regardless of the dryness of, or infiltration of fluids to the inside of the flat adapter section. In fact, a substantially unobstructed vision clarity is achieved whether the contacting flat surfaces of the windows 69 and 95 are wet or dry.

In some surgical applications, some relatively hard particles can become entrapped between the two contacting flat surfaces of the windows 69 and 95. Such particles can cause scratching as well as possible cracking of the windows. Therefore, the windows 69 and 95 can be fabricated of a suitable hard-polished crystalline material such as sapphire, in order to prevent fracturing or scratching due to the entrapped dust or like hard particles.

It is sometimes possible to apply a relatively excessive compression force on the windows 69 and 95 when assembling the adapter assembly 10. Thus, it might be desirable to add and to seat a resilient annular seal member between the window 95 and the shoulder 99, in order to provide the necessary cushioning effect thereto, and to dampen the excessive compression force therebetween. Furthermore, such a resilient seal would tend to compensate for small errors in parallelism between the two contiguous window surfaces. The seal member is generally indicated in phantom lines at 110. Such arrangement can further reduce fracturing or scratching of the windows 69 and 95 due to the presence of foreign hard particles therebetween.

Another contributory source of scratching in a glass-on-glass interface is the rotary movement of the contacting surfaces of the windows 69 and 95 relative to one another. Therefore, in order to minimize if not eliminate such scratching effect, a coupling mechanism generally indicated at 115 causes the ocular adapter 27 to be drawn axially linearly without rotation into mating relationship with the endoscope-engageable portion 30.

The coupling mechanism 115 generally includes a tubular outer retaining ring 120 which is hollow throughout its axial length, and which engages the outer periphery of the flared annular section 90 and of the adjacent portion of the chassis 88. The outer retaining ring 120 rotates freely about the flared annular section 90 and has a corrugated section 122 for facilitating its manual rotation.

The outer retaining ring 120 includes at its inner periphery two helical slots, one of which is indicated by 125, which generally contours the outer periphery of the flared section 90. The slots 125 are adapted to receive the studs, such as the stud 75, of the ocular adapter 27, through a pair of elongated openings, one of which is depicted by 130 and 133 in the flared section 90. The openings 130 and 133 are substantially symmetrical relative to the axis of the chassis 88 and are adapted to guide the studs linearly axially from the terminal end 100 towards the shoulder 99.

The openings 130 and 133 are generally identical. Therefore, only the opening 130 will be described hereinafter in greater detail. The opening 130 extends linearly from the terminal open end 100 of the chassis 88 to about threequarters of the depth of the flared section 90. The opening 130 terminates in a substantially semi-circular section 135 for receiving the pin or stud 75. The width of the opening 130 is commensurate with the dimension of the stud 75 so as to minimize the lateral non-axial movement thereof. The helical slot 125 commences at about the terminal open end 140 of the outer retaining ring 120 and terminates at a relatively short distance from the shoulder 99.

Therefore, in order to couple the endoscope-engageable portion 30 with the ocular adapter 27, the studs (i.e. the stud 75) of the ocular adapter 27 are first engaged to the corresponding slots 130 and 133. The outer retaining ring 120 is then rotated in a predetermined direction, such as the clockwise direction, so as to cause the helical slot 125 to advance the ocular adapter 27 linearly axially inside the flared section 90 until the window 69 abuts the window 95.

The outer retaining ring 120 forms an internal annular chamber 144 with the chassis 88. The chamber 144 houses an annular spring 146, which is generally known as the Belleville washer or waffle spring for providing the chassis 88 with a certain degree of axial resiliency.

Considering now the intermediate or focusing portion 33 in greater detail with respect to FIGS. 6 and 8, it generally includes a hollow front bayonet capture ring 151, which is substantially conical in design. The front bayonet capture ring 151 contours a portion of the outer periphery of the chassis 88 and has its larger base 153 abut the outer retaining ring 120. It is rigidly affixed to the chassis 88 by means of adhesive or interference fit.

A hollow annular focusing ring 155 is disposed adjacent to the rear bayonet capture ring 151 and rotatably contours a part of the chassis 88. The focusing ring 155 includes an internal helical opening 162 for providing an axial focusing path of travel for an internal optical lens 156. A lens sleeve 160 is disposed totally within the chassis 88 and is slidingly secured to the focusing ring 155 for focusing the virtual image at the proximal end 20 onto a pickup device such as a CCD sensor (not shown) of the camera head 16.

A longitudinal axial focusing slot 170 extends along the chassis 88 generally intermediate the lens sleeve 160 and the focusing ring 155 for enabling a pin 173 to pass therethrough in order to interconnect the lens sleeve 160 and the focusing ring 155. In this regard, and as illustrated in FIG. 8, the lens sleeve 160 has a generally cylindrical shape, and it is hollow throughout its entire axial length. The lens sleeve 160 includes a plurality of spaced-apart similar radially extending bores, such as the bores 180, 181, 182 and 183, for enabling a selective positioning of the lens 156 relative to the video camera head 16.

In this manner, the pin 173 can fit snugly frictionally within either one of the bores 180 through 183. The selection of the corresponding bores depends upon the focal lens of the lens 160. For instance, if the lens 156 were a 25 mm lens, the bore 181 would then be selected and aligned with the helical slot 163 by the insertion of the pin 173 therebetween, through the focusing slot 170 of the chassis 88.

Similarly, if the lens 156 were a 32 mm, another bore, such as the bore 183 would then be selected for being coupled to the focusing ring 155. However, if the lens 156 were a 38 mm lens, then the lens sleeve 160 could be rotated by 180° so as to have the lens 156 face the endoscope-engageable portion 30, rather than the camera adapter 38, as illustrated in FIG. 6. Thus, the endoscopic adapter 10 enjoys a flexible and wide focusing range while still maintaining a compact and lightweight construction.

The focusing ring 155 has a generally corrugated outer surface for facilitating its manual axial rotation. A pair of O-ring seals 190 and 193 is disposed on the opposite sides of the focusing ring 155 for providing a liquid-tight seal, while still permitting the focusing ring 155 to rotate freely. The outer retaining ring 120, the focusing ring 155, as well as the lens sleeve 160 are made of suitable non-corrosion material such as stainless steel.

The intermediate or focusing portion 33 further includes a hollow rear bayonet capture ring 200 which is disposed adjacent to the focusing ring 155, and which contours a part of the chassis 88. The rear capture ring 200 is generally similar in structure and composition to the rear bayonet capture ring 151 and is disposed symmetrically thereto, relative to the plane of symmetry of the focusing ring 155. It is similarly rigidly affixed to the chassis 88.

Considering now the camera engageable portion 38 in greater detail with respect to FIGS. 4 and 6, it generally includes an endoscope adapter bayonet shell 201 which is generally hollow throughout its entire axial line, and which mates rotatably with the opposite free end 202 of the chassis 88. The bayonet shell 201 includes a corrugated surface 203 for facilitating its rotation about the chassis 88. The bayonet shell 201 abuts the rear bayonet capture ring 200 in a rotatable relationship therewith.

An endoscope bayonet 205 is fitted frictionally within the inner periphery of the shell 201 and includes an annular ring 206. The ring 206 is generally circular in cross section and is hollow throughout its axial length. A relatively short annular shoulder 207 extends integrally orthogonally from the ring 206 at a substantially right angle to the axis of the chassis 88.

As illustrated in FIG. 6, a substantially Y-shaped annular seal 210 has its annular light 211 inserted between the free end 202 of the chassis 88 and the shell 201 in such a way as to be rigidly, frictionally affixed to the chassis and rotatably connected to the bayonet shell-bayonet 201, 205 assembly. The seal 210 has an annular generally circularly shaped channel 215 for housing an O-ring seal 216.

The ring 206 of the bayonet 205 has a plurality of spaced-apart bayonet slots, such as the slots 220, 221 and 222 for cooperating and mating with a corresponding number of pins, such as the pin 225, which protrude axially outwardly from the camera head 16 (FIG. 2). The bayonet slots 220 through 222 are generally identical, and therefore only the bayonet slot 220 will hereinafter be described in greater detail with respect to FIG. 6.

The bayonet slot 220 is generally L-shaped and has a generally axial opening 230 which helps guide the corresponding pin 235 into an angularly disposed elongated generally peripheral opening 231. The opening 231 is slightly directed inwardly towards the focusing portion 33. In this manner, when the pin 225 engages the bayonet slot 220, the camera head 16 is forced gradually inwardly into engagement with the bayonet 205 until the pin 225 reaches a detente portion 233.

The detente portion 233 is generally angularly outwardly disposed relative to the opening 231, and it is generally circular in shape so as to receive and to retain the pin 225 in secure engagement. The detente portions, such as the detente portion 233, further provide an audible feedback in the form of a clicking signal to the user in order to indicate that the camera head 16 has properly engaged adapter assembly 10.

The bayonets slot 220 through 222 are not equidistantly spaced apart from one another for the purpose of providing a visual feedback signal of the proper engagement of the camera head 16 and the endoscope adapter assembly 10. In this regard, the shell 201 has a mark 260 which corresponds to, and which becomes aligned with, a mark (not shown) on the camera head 16 when the pins, such as the pin 225, mate properly with the corresponding pre-assigned bayonet slots 220 through 222.

Optionally, the ocular adapter 27 can be replaced with an eyepiece adapter which engages the endoscope-engageable portion 30 in a similar manner as does the ocular adapter 27.

While a particular embodiment of the present invention has been disclosed, it is to be understood that various different modifications are possible and are contemplated within the true spirit and scope of the appended claims. There is no intention, therefore, of limitation to the exact abstract or disclosure herein presented.

What is claimed is:

1. An endoscopic adapter assembly for coupling a video camera head and an endoscope having a proximal end, comprising in combination:
   a. ocular adapter means for engaging the proximal end of the endoscope;
   b. endoscope-engageable means for engaging said ocular adapter means;
   c. means for focusing being rotatably secured to said endoscope-engageable means;
   d. camera-engageable means being rotatably secured to said focusing means, for connecting said focusing means to the camera head;
   e. said ocular adapter means including a window; and
   f. said endoscope-engageable means including a window being aligned with, and facing said window of said ocular adapter means for maintaining glass-on-glass contact therewith.

2. An endoscopic adapter assembly as defined in claim 1 wherein said endoscope-engageable means includes coupling means for drawing said ocular adapter means axially linearly into a mating relationship therewith.

3. An endoscopic adapter assembly as defined in claim 2, wherein said ocular adapter means includes an elongated tubular chassis which is hollow throughout its axial length.

4. An endoscopic adapter assembly as defined in claim 3, wherein said chassis is made of suitable noncorrosive material.

5. An endoscopic adapter assembly as defined in claim 3, wherein said chassis includes an internally threaded portion, for engaging threadably the proximal end.

6. An endoscopic adapter assembly as defined in claim 5, wherein a pair of similar spaced-apart pins extend radially outwardly from said chassis for mating with said endoscope-engageable portion.

7. An endoscopic adapter assembly as defined in claim 2, further comprising an elongated tubular chassis which is hollow throughout its axial length.

8. An endoscopic adapter assembly as defined in claim 7, wherein said chassis is made of suitable non-corrosive material.

9. An endoscopic adapter assembly as defined in claim 7, wherein said chassis includes a flared annular section which is generally complementary sized and dimensioned to receive a forward section of said ocular adapter chassis.

10. An endoscopic adapter assembly as defined in claim 9, wherein said window of said ocular adapter is transversely disposed at a substantially right angle to the axis of said ocular adapter.

11. An endoscopic adapter assembly as defined in claim 9, wherein said window of said endoscope-engageable means is disposed transversely at a substantially right angle to the axis of said chassis.

12. An endoscopic adapter assembly as defined in claim 11, wherein said ocular adapter window is made of hard polished crystalline material.

13. An endoscopic adapter assembly as defined in claim 12, wherein said ocular adapter window is made of sapphire.

14. An endoscopic adapter assembly as defined in claim 11, wherein said window of said endoscope-engageable means is made of hard polished crystalline material.

15. An endoscopic adapter assembly as defined in claim 14, wherein said window of said endoscope-engageable means is made of sapphire.

16. An endoscopic adapter assembly as defined in claim 7, wherein said endoscope-engageable means includes a coupling mechanism for mating with said ocular adapter pins.

17. An endoscopic adapter assembly as defined in claim 16, wherein said coupling mechanism generally includes a tubular outer retaining ring which is hollow throughout its entire axial length, and which engages rotatably about the periphery of said flared annular section of said chassis.

18. An endoscopic adapter assembly as defined in claim 17, wherein said outer retaining ring includes a corrugated section for facilitating its manual rotation.

19. An endoscopic adapter assembly as defined in claim 18, wherein said outer retaining ring includes an internal helical slot which contours the outer periphery of said flared annular section for receiving said ocular adapter studs.

20. An endoscopic adapter assembly as defined in claim 19, wherein said flared section includes a pair of spaced-apart generally diametrically disposed elongated axial openings, for receiving said ocular adapter studs.

21. An endoscopic adapter assembly as defined in claim 20, wherein said focusing means includes a hollow rear bayonet capture ring which contours a portion of said endoscope-engageable means chassis.

22. An endoscopic adapter assembly as defined in claim 21, wherein said focusing means includes an annular focusing ring disposed adjacent to said rear bayonet capture ring and which rotatably contours a part of said endoscope-engageable means chassis.

23. An endoscopic adapter assembly as defined in claim 22, wherein said focusing means includes a lens sleeve which is disposed within said chassis of said endoscope-engageable means.

24. An endoscopic adapter assembly as defined in claim 23, wherein said focusing ring includes an internal helical opening for providing an axial focusing path of travel for said lens sleeve.

25. An endoscopic adapter assembly as defined in claim 24, wherein said focusing means includes a pair of spaced-apart, generally parallel seals.

26. An endoscopic adapter assembly as defined in claim 25, wherein said focusing means includes a front bayonet capture ring disposed adjacent the said focusing ring and which contours a part of said chassis of said endoscope-engageable means.

27. An endoscopic adapter assembly as defined in claim 26, wherein said rear bayonet capture ring, said front bayonet capture ring and said focusing ring are made of suitable non-corrosive material.

28. An endoscopic adapter assembly as defined in claim 21, wherein said camera-engageable means includes an endoscope adapter bayonet shell which mates rotatably with said chassis of said endoscope-engageable means.

29. An endoscopic adapter assembly as defined in claim 28, wherein said endoscope adapter bayonet shell includes a corrugated surface for facilitating its rotation.

30. An endoscopic adapter assembly as defined in claim 29, wherein said camera-engageable means further includes an endoscopic adapter bayonet which is fitted frictionally within the inner periphery of said shell.

31. An endoscopic adapter assembly as defined in claim 30, wherein said camera-engageable means includes an annular seal.

32. An endoscopic adapter assembly as defined in claim 30, wherein said bayonet includes a plurality of spaced-apart bayonet slots, and wherein the camera head includes a corresponding number of outwardly extending spaced-apart studs, for mating with said bayonet slots.

33. An endoscopic adapter assembly as defined in claim 32, wherein said bayonet slots are substantially identical in design and dimension.

34. An endoscopic adapter assembly as defined in claim 33, wherein each one of said bayonet slots includes a detente portion for providing a human audible signal indicative of the proper engagement between said camera-engageable means and the camera head.

35. An endoscopic adapter assembly as defined in claim 34, wherein said bayonet slots are not equidistantly spaced apart from one another, for the purpose of providing a human visual feedback signal indicative of the proper engagement and alignment of the camera head and said camera-engageable means.

* * * * *